(12) United States Patent
Van Vorhis

(10) Patent No.: US 8,942,785 B2
(45) Date of Patent: Jan. 27, 2015

(54) SELECTABLE ORIENTATION BENT TIP CALIBRATION-FREE PROBE

(75) Inventor: Robert Van Vorhis, Davis, CA (US)

(73) Assignee: Mako Surgical Corporation, Fort Lauderdale, FL (US)

( * ) Notice: Subject to any disclaimer, the term of this patent is extended or adjusted under 35 U.S.C. 154(b) by 0 days.

(21) Appl. No.: 13/313,527

(22) Filed: Dec. 7, 2011

(65) Prior Publication Data

US 2013/0150708 A1    Jun. 13, 2013

(51) Int. Cl.
*A61B 5/107* (2006.01)

(52) U.S. Cl.
USPC .......................................................... 600/424

(58) Field of Classification Search
USPC ................... 600/424, 426, 429, 587; 606/130
See application file for complete search history.

(56) References Cited

U.S. PATENT DOCUMENTS

| 4,753,641 | A | * | 6/1988 | Vaslow | 604/274 |
| 6,036,645 | A | * | 3/2000 | Drost et al. | 600/459 |
| 6,246,900 | B1 | * | 6/2001 | Cosman et al. | 600/426 |
| 6,974,416 | B2 | | 12/2005 | Booker et al. | |

* cited by examiner

*Primary Examiner* — Michael Rozanski
(74) *Attorney, Agent, or Firm* — Miller, Matthias & Hull LLP

(57) ABSTRACT

A probe is provided. The probe may include a shaft portion rotatably attachable to a position sensing device, a nonlinear portion at least partially removed from a center axis of the shaft portion, and a tip disposed at a distal end of the nonlinear portion and positioned on the center axis. The nonlinear portion may be selectably rotatable about the center axis to one of a plurality of rotational orientations. The tip may have a substantially constant position relative to the position sensing device.

20 Claims, 4 Drawing Sheets

SELECTABLE ORIENTATION BENT TIP CALIBRATION-FREE PROBE

TECHNICAL FIELD

The present disclosure relates generally to surgical devices, and more particularly, to bent tip probes for collecting positioning data of anatomic surfaces.

BACKGROUND

Minimally invasive surgery (MIS) is commonly known in the art as surgical procedures that are performed through incisions that are considerably smaller than incisions used in traditional surgical approaches. The less invasive nature of MIS procedures presents several advantages which promote the continued use thereof. Among other things, the smaller incisions of MIS procedures may help minimize trauma to soft tissue, reduce post-operative pain, promote earlier mobilization, and shorten hospital stays as well as rehabilitation times.

However, the reduced incision size of MIS procedures tends to limit the surgeon's ability to access or view anatomic surfaces within the region of interest. To overcome such limitations, the surgeon may use a bent tip probe, such as the probe P shown in FIG. 1, which can be inserted into the incision and used to gain better access to anatomic surfaces within the exposure surrounding the particular region of interest. In particular, the tip at the proximal end of the probe may be fitted with an optoelectronic transducer or any other means capable of detecting positional changes in the anatomic surface relative to the probe tip and generating electronic pulses or signals corresponding thereto. As shown in FIG. 1, for example, a bent tip probe P may be used to reach anatomic surfaces S having a normal axis N that is perpendicular to the direction of surgical access $D_{access}$. As further shown in FIG. 2, for example, in a configuration adapted for use with an optical position transducer, a bent tip probe P may be used to gain access to anatomic surfaces S having a normal axis N that is parallel but in opposition to the direction of the line-of-sight $D_{sight}$.

Bent tip probes may generally be used to register the pose, such as the position and orientation, of a computational representation or digitized model of an anatomic region obtained from medical imaging devices to the actual pose of the corresponding anatomic region within a surgical workspace. In particular, the distal end of the probe may be coupled to a position sensing device which may employ, for instance, an array of optically detectable markers, a mechanical tracking arm, an electromagnetic tracking system, or any other suitable means configured to track the position of the probe tip relative to the position sensing device. By tracking the probe tip and using other known relationships between the position sensing device and the surgical setting, quantitative points for the registration between the digitized anatomy and the actual anatomy may be obtained. Based on the quantitative points, the surgeon may be able to register and synchronize the pose of the digitized anatomy with its actual counterpart prior to or during surgical procedures.

In alternate applications, the bent tip probe may be used to provide a more detailed image representation or model of a particular anatomic region that may otherwise be difficult to view without making additional incisions. In such applications, the distal end of the probe may be attached to a surgical tool, such as a tool that may be used in conjunction with tracking devices, haptic or force-feedback devices, imaging devices, and/or any other computer-assisted device designed to assist a surgeon with surgical planning and/or surgical navigation. A computer system associated with the surgical tool may receive the signals generated by the transducer in response to detected changes proximate the probe tip, and use the corresponding positioning data to generate digitized models of the surfaces within the anatomic region for the surgeon to use as reference.

Although bent tip probes may provide some useful insight on anatomic surfaces that are situated in areas of limited access, there is still room for improvement. For instance, as bent tip probes are attached to a position sensing device or a surgical tool, the positional flexibility or the range of movement of the probe is limited to that of the device or tool to which it is rigidly coupled. In order for a surgeon to access all of the relevant anatomic surfaces of a particular region of interest, the surgeon often needs to readjust the angle and/or direction of the probe tip, thus requiring readjustment of the rotational position of the probe relative to the surgical tool. However, as the consistency of the positioning data captured at the probe tip is dependent on the position of the probe tip relative to the surgical tool, a calibration for an arbitrarily bent tip probe is required after each adjustment. Repeated probe calibrations, especially for each of several anatomic surfaces within one region of interest, can be quite cumbersome, time consuming and cause undesirable interruptions.

Furthermore, proper use of bent tip probes currently available in the art requires consideration for two generally independent orientation constraints, for instance, constraints associated with the probe tip and constraints associated with the sensor end of the probe. Optimal orientation of the probe tip may require the tip to be normal to the digitized surface. Optimal orientation of the sensor end may be specific to the type of sensing scheme being employed. A sensing scheme using an array of markers, for example, may require the line-of-sight to be oriented toward the optical sensor. A mechanical tracking arm employing an instrumented spatial link may be constrained by simple kinematics of the probe itself. Rotation of the handle may also be another consideration for setting the orientation of the probe. The multitude of such constraints and the interdependencies therebetween increases the complexity of each calibration and adjustment, thus increasing the risk to inaccuracies and consuming more time.

Accordingly, there is a need for a simplified surgical device that can be used to facilitate MIS procedures without requiring multiple calibrations per use. Moreover, there is a need for a surgical probe that can gain access to more anatomic surfaces of a particular region of interest from a single pre-calibration without compromising the accuracy of the positioning data collected and eliminating interruptions or delays. There is also a need for a probe that enables user-selectable orientations with substantially less variables and constraints while preserving overall utility and functionality. Specifically, there is a need to provide a probe with a tip position that is independent of the orientation of the probe.

SUMMARY OF THE DISCLOSURE

In one aspect of the present disclosure, a probe is provided. The probe may include a shaft portion rotatably attachable to a position sensing device, a nonlinear portion at least partially removed from a center axis of the shaft portion, and a tip disposed at a distal end of the nonlinear portion and positioned on the center axis. The nonlinear portion may be selectably rotatable about the center axis to one of a plurality of rotational orientations. The tip may have a substantially constant position relative to the position sensing device.

In a refinement, the nonlinear portion may be configured such that the tip aligns with the center axis independent of the orientation of the nonlinear portion.

In another refinement, the tip may be adapted to collect positioning data of an anatomic surface.

In another refinement, the tip may include a digitizing point configured to digitize anatomic surfaces for registration to computationally represented anatomic surfaces.

In another refinement, the tip may be configured as a sphere having a spherical center disposed on the center axis.

In yet another refinement, the tip may be configured to receive an optoelectronic position transducer.

In another aspect of the present disclosure, a surgical device is provided. The surgical device may include a handle rotatably attachable to a position sensing device, and a probe coupled to the handle. The probe may include a nonlinear connector and a tip. The nonlinear connector may be rotatable about a center axis to one of a plurality of rotational orientations, while the tip may have a substantially constant position relative to the position sensing device.

In a refinement, the nonlinear connector may be bent at least once along a length thereof and the tip may be configured to align with the center axis independent of the rotational orientation of the nonlinear connector.

In another refinement, the tip may be configured as a sphere having a spherical center disposed on the center axis.

In another refinement, the handle may be coupled to the position sensing device through a revolute joint and the rotational orientation of the nonlinear connector may be selectable through rotation of the handle.

In a related refinement, an initial calibration of the probe may be maintained through a plurality of different rotational orientations.

In another refinement, the tip may include a digitizing point configured to digitize anatomic surfaces for registration to computationally represented anatomic surfaces.

In yet another refinement, the probe may be fitted with an array of markers.

In yet another aspect of the present disclosure, a surgical system is provided. The surgical system may include a position sensing device, a probe coupled to the position sensing device, and a computer system in communication with the probe. The probe may include a nonlinear connector and a tip configured to collect positioning data from an anatomic surface. The nonlinear connector may be rotatable about a center axis to one of a plurality of rotational orientations relative to the position sensing device. The tip may have a substantially constant position relative to the position sensing device. The computer system may be configured to receive the positioning data from the tip, and digitize points of the anatomic surface based on the positioning data.

In a refinement, the probe may be configured such that the tip aligns with the center axis independent of the rotational orientation of the nonlinear connector.

In another refinement, the computer system may be configured to register the digitized points of the anatomic surface to a computational representation of the anatomic surface based on the positioning data.

In a related refinement, the computer system may be configured to synchronize a spatial pose of the computational representation of the anatomic surface to an actual pose of the anatomic surface.

In another refinement, the position sensing device may employ an array of markers to track the probe.

In another refinement, the position sensing device may employ a mechanical tracking arm for tracking the probe.

In yet another refinement, the tip may be configured as a sphere having a spherical center disposed on the center axis.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Although the following disclosure may make references to specific anatomic regions of the body, it should be understood that the subject matter described herein is applicable to other relevant regions of the anatomy.

Figure 1:
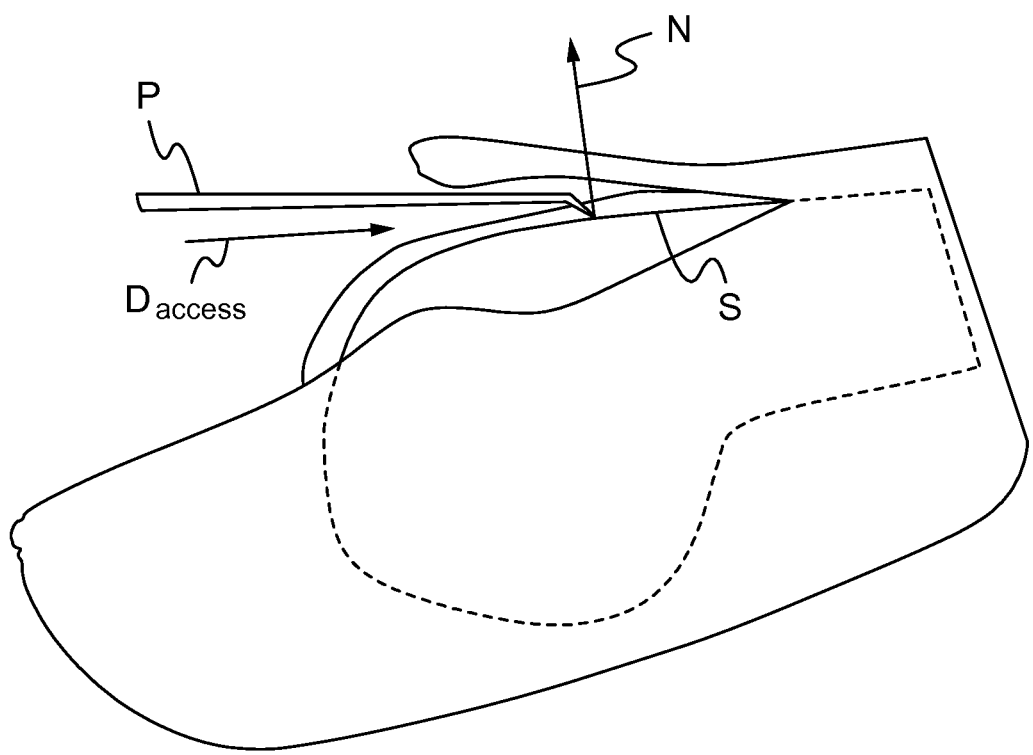
FIG. 1 is a diagrammatic view of a prior art bent tip probe in use.
Figure 2:
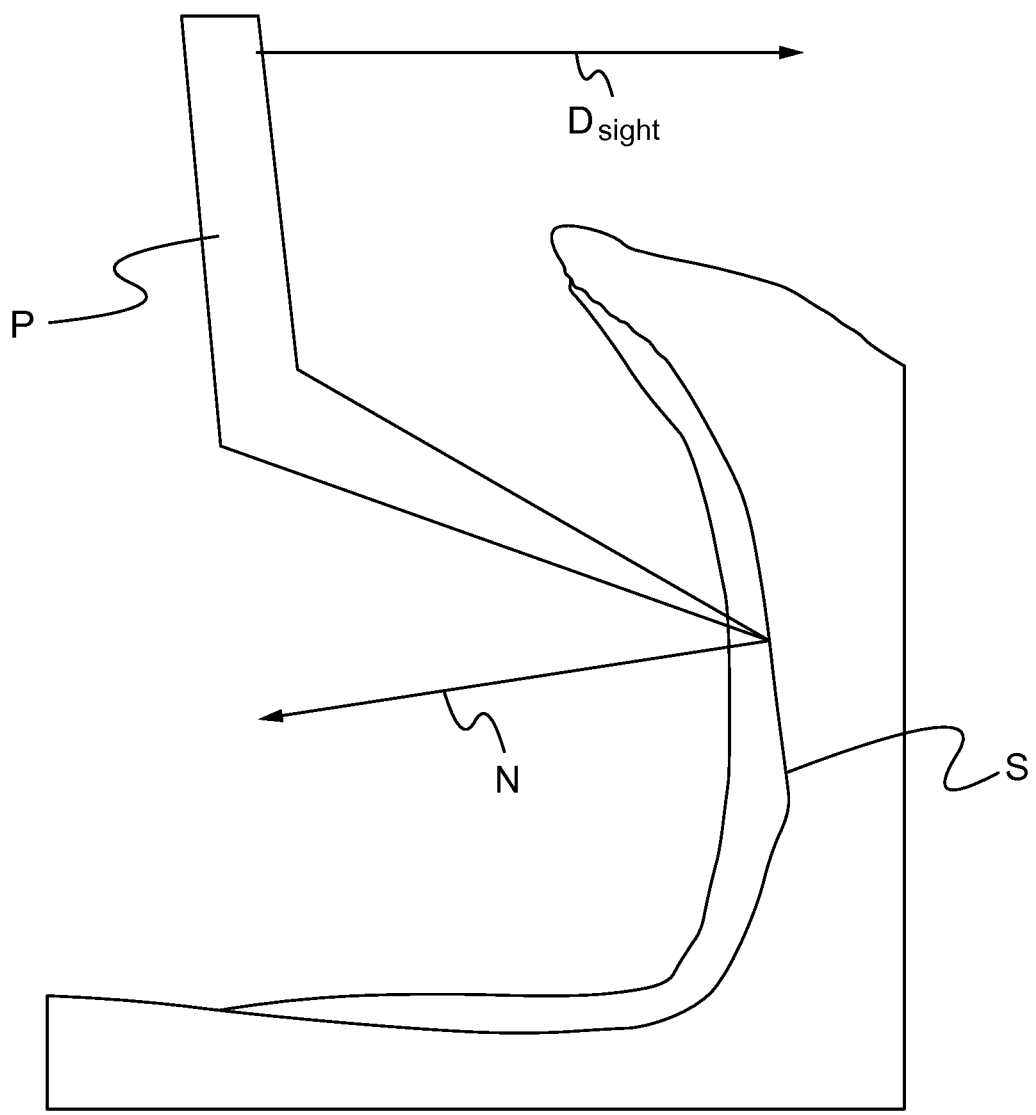
FIG. 2 is a diagrammatic view of another prior art bent tip probe in use.
Figure 3:
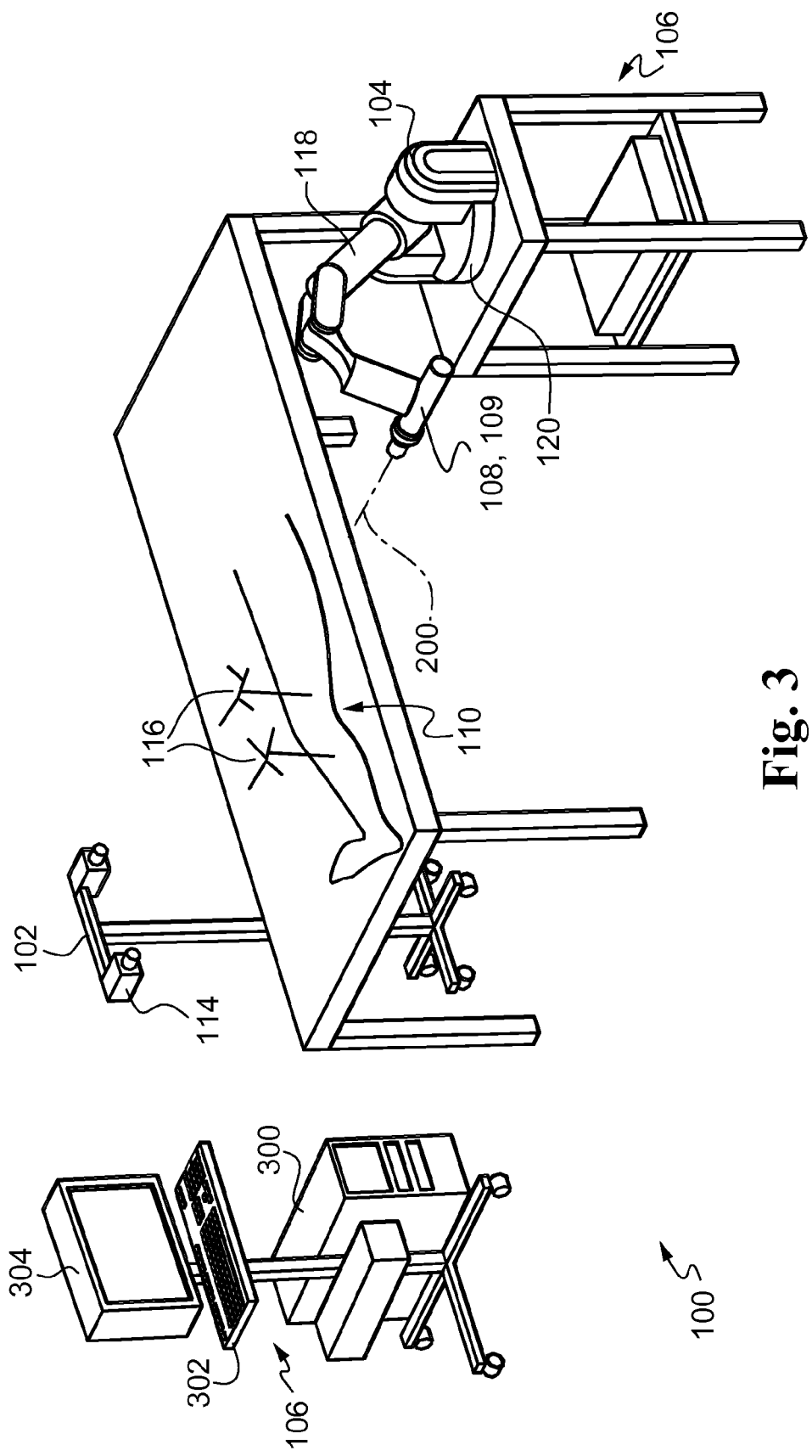
FIG. 3 is a graphical view of an exemplary surgical system.

Referring to FIG. 3, one exemplary environment or surgical workspace within which a surgical system 100 may be used is provided. Depending on the desired application, the environment may generally include any one or more of a tracking device 102, a haptic device 104, a computer system 106, and a position sensing device 108. In more typical applications, the surgical system 100 may be used to digitize points of surfaces of the actual anatomy and register the points on, for instance, a model of the anatomy, to establish a computational awareness of the actual position and/or orientation of the anatomy relative to the surgical workspace. In other alternative applications, the position sensing device 108 may further include a surgical tool 109 by which the surgical system 100 may be used as an aid for planning and/or performing surgical work upon an anatomic region or surgical volume 110, for example, a leg as shown in FIG. 3. More specifically, the tracking device 102 and the haptic device 104 may be used to assist the user in guiding the surgical tool 109 within the surgical volume 110, while the computer system 106 may be used to manage the overall operation of the surgical system 100. Actual work on or within the surgical volume 110 may be performed by controlling and manipulating the surgical tool 109 during surgery, surgical planning and/or surgical navigation, as described, for example, in U.S. patent application Ser. No. 11/357,197 (Pub. No. 2006/0142657), filed Feb. 21, 2006, which is hereby incorporated by reference.

The tracking device 102 may include means for tracking movement within the anatomic region of interest or surgical volume 110. In particular, the tracking device 102 may include a detector 114 and spatially detectable tracking arrays 116, such as reflective disks, or the like, that are affixed about the surgical volume 110. By tracking the tracking arrays 116, the detector 114 may be able to track any significant movement within the surgical volume 110 and dynamically compensate for such movement. The tracking device 102 may additionally include apparatus, such as unique identifiers positioned on or within the surgical tool 109 of the position sensing device 108, for tracking the spatial position and orientation of the surgical tool 109 relative to the tracking arrays 116 and the surgical volume 110. Alternatively, information provided by the tracking device 102 may be used in conjunction with the net displacement of the surgical tool 109 as detected by the haptic device 104 in order to determine the spatial location of the surgical tool 109 relative to the surgical volume 110. Based on such tracking techniques and using known geometric relationships between the surgical volume 110 and the tracking arrays 116, the surgical system 100 may be able to track the spatial position and orientation, as well as the velocity and/or acceleration, of the surgical tool 109 and the position sensing device 108 relative to the tracking arrays 116 and the surgical volume 110.

The haptic device 104 and the surgical tool 109 coupled thereto may be manipulated by the user while performing surgical procedures upon the surgical volume 110. As shown in FIG. 3, for example, the haptic device 104 may include a haptic arm 118 that is movable relative to its base 120 and adapted to transmit haptic feedback, or tactile stimulations such as vibrations, pulses, force and/or torque feedback, to the user. Additionally, the joints and/or hinges of haptic device 104 may be fitted with position sensors, encoders, or the like, configured to communicate data pertaining to the spatial position, orientation, velocity and/or acceleration of the surgical tool 109 relative to at least the base 120 thereof. The haptic device 104 may further aid user manipulation of the surgical tool 109 by selectively providing haptic feedback corresponding to different regions of interest within the surgical volume 110 that the surgical tool 109 is approaching.

A spatial mapping of the regions of interest within the surgical volume 110 as well as their respective boundaries may be observed using the computer system 106 and derived based on a compilation of medical images and input from the surgeon during the pre-operative and/or intra-operative planning. The medical images may be provided by medical imaging devices commonly used in the art, such as computed tomography (CT) devices, magnetic resonance imaging (MRI) devices, fluoroscopic devices, ultrasound devices, and the like. Based on the mapped locations of the regions of interest within the surgical volume 110, the computer system 106 may communicate the boundaries of the regions to the haptic device 104 in terms of control parameters or limits within which the haptic arm 118 and the surgical tool 109 are permitted to move. For example, the haptic device 104 may limit the user's ability to physically move the surgical tool 109 beyond the boundaries of a particular region by depowering or electromechanically resisting manipulation of the haptic arm 118 and the associated surgical tool 109 in a particular direction or beyond a particular range of motion. The haptic device 104 may additionally provide feedback in the form of tactile vibrations, pulses, force feedback, torque feedback, and the like, configured to aid the user in distinguishing between the different regions within the surgical volume 110.

Figure 4:
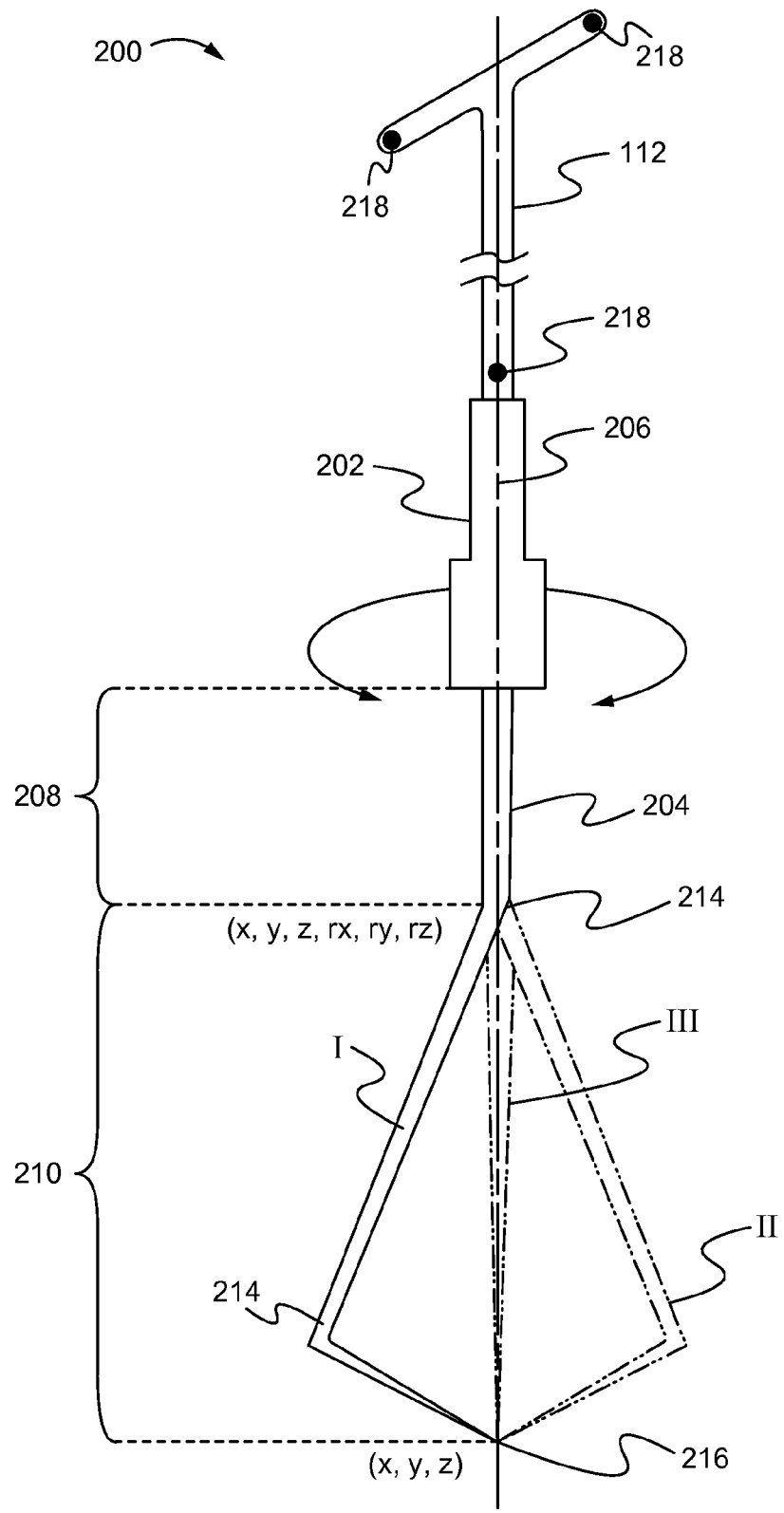
FIG. 4 is a graphical view of an exemplary surgical device having a bent tip probe that is constructed in accordance with the teachings of the present disclosure.

Turning now to FIG. 4, one exemplary embodiment of a surgical device 200 that may be used with the surgical system 100 of FIG. 3 is provided. In particular, the surgical device 200 may essentially include a handle 202 and a probe 204 adapted to collect positioning data or digitize points of anatomic surfaces within surgical volumes 110 that may otherwise be difficult to access, for example, during MIS procedures. As shown, the handle 202 may be removably coupled to the position sensing device 108 of FIG. 3, or in alternative configurations, to a surgical tool 109 of the position sensing device 108. The handle 202 may further include one or more revolute joints about which the handle 202 may be rotatably adjusted relative to the position sensing device 108. The bent tip probe 204 of the surgical device 200 may generally extend along a center axis 206 that is defined by the handle 202 and/or the surgical tool 106. Moreover, the distal end of the probe 204 may be rigidly coupled to the handle 202 such that a rotation of the handle 202 corresponds to a direct rotation of the probe 204. Accordingly, the handle 202 and the probe 204 may be selectable to any one of a plurality of rotational orientations about the center axis 206 and relative to the position sensing device 108.

Still referring to FIG. 4, the probe 204 may be bent at least once along the length thereof so as to define a nonlinear connector including, for example, a shaft portion 208 and a nonlinear portion 210. The shaft portion 208 of the probe 204 may be configured to extend along the center axis 206 and be rigidly coupled to the handle 202. The nonlinear portion 210 may include a first bend 212 through which the probe 204 is at least partially removed from the center axis 206, as well as a second bend 214 through which the probe 204 is redirected toward and ultimately rejoined with the center axis 206. Although the nonlinear portion 210 of FIG. 4 may be shown to include two angled bends 212, 214, both of which are formed within a single plane that intersects the center axis 206, alternative modifications may provide a single bend or more than two bends that are disposed along the body of the probe 204. In further modifications, the probe 204 may include a plurality of bends which are not necessarily coplanar, or formed within the same plane. In still further modifications, the bends may be rounded or curved rather than angled. In all modifications, however, the nonlinear portion 210 may be configured such that a tip 216 of the probe 204 remains positioned on the center axis 206 for all rotational orientations. As illustrated in FIG. 4, for example, the probe 204 may be configured such that the position of its probe tip 216 relative to the handle 202 and the position sensing device 108 remains unchanged in any of the three different rotational orientations I, II, III. Specifically, the position of the probe tip 216 at any particular instance may be represented as tip position (x, y, z) relative to a particular anatomy or any other common frame of reference within the surgical workspace. The orientation of the nonlinear connector, extending from the probe tip 216 to the handle 202, may be represented as a probe orientation (x, y, z, rx, ry, rz) relative to a shared frame of reference. The probe 204 may be configured such that for any particular probe orientation (x, y, z, rx, ry, rz), the tip position (x, y, z) remains constant, and thus, independent of rotational orientation. In certain embodiments, the sensing mechanism or scheme for tracking the probe tip 216 may depend on, for instance, a line-of-sight, and thus, may require consideration for not only on the spatial position of the probe tip 216 but also the rotational orientation of the probe tip 216. In such configurations, additional transductions relating to the probe orientation (x, y, z, rx, ry, rz) may be required. For example, the surgical system 100 may need to additionally consider the orientation of the probe 204 or the nonlinear connector, radial and/or longitudinal forces, or the like. In still further modifications, the probe tip 216 may be configured in the form of a sphere having a center disposed on the center axis 206.

The probe tip 216 of the surgical device 200 of FIG. 4 may be used in conjunction with the position sensing device 108 so as to digitize points of anatomic surfaces and to establish a synchronization or registration between the digitized points and corresponding points on a digitized model of the anatomic region. By registering actual points of the anatomy to digitized points of a computational model of the anatomy, the computer system 106 may be able to display a model of the anatomic region of interest in a spatial pose, or a position and orientation, which more closely corresponds to the actual pose of the anatomy relative to the surgical workspace. The surgical device 200 may also be used to indicate specific portions of the anatomy other than bone, such as cartilage, and the like, which may not have been sufficiently imaged or modeled pre-operatively. In such a way, the surgical device 200 may be configured to generate more complete models of the bone as well as other relevant anatomic features for visualization purposes, haptic computations, and the like. Specifically, the probe tip 216 may be configured such that, as it is moved along an anatomic surface within the surgical volume 110, optical, acoustic, or other sensory data corresponding to the changes in the position of the anatomic surface is collected and communicated to the relevant computer system 106 associated therewith. For example, the probe tip 216 may be fitted with an array of markers, an optoelectronic transducer, or other sensory means that enables the computer system 106 to digitize points on actual anatomic surfaces to a corresponding computational model thereof. The sensing mechanisms employed may generate electronic signals corresponding to changes in the proximity of the anatomic surface relative to the probe tip 216. The electronic signals may be transmitted wirelessly or through electrical wires, fiber optics, communication cables, or the like, that may be routed from the probe 204 to the associated computer system 106.

The position sensing device 108 may use any one or more of a plurality of schemes for tracking the position of the surgical device 200 and the probe tip 216 relative to the anatomy and/or a common frame of reference within the surgical workspace. For instance, the position sensing device 108 may track the surgical device 200 using an array of markers 218, such as reflective disks responsive to light emitted by the tracking device 102, or the like, disposed at known locations on the exterior of the surgical device 200. Based on tracking data obtained from the position sensing device 108 and the tracking device 102, the associated computer system 106 may be able to determine the position of the surgical device 200 relative to an anatomic region and/or a common frame of reference within the surgical workspace at any point in time. The surgical device 200 may also be used in conjunction with a mechanical tracking arm, or the like, configured to track the position of the probe tip 216 using known or fixed positional relationships between the probe 204 and the position sensing device 108. Moreover, based on the detected movements or kinematic changes in the position sensing device 108, the associated computer system 106 may be able to track the position of the surgical device 200 and the probe tip 216 relative to the anatomic region and/or a common frame of reference within the surgical workspace. In alternative modifications, the position sensing device 108 may also employ electromagnetic tracking schemes, triangulation, or any other suitable means for tracking the surgical device 200 and/or the probe tip 216 relative to a particular anatomic region.

The computer system 106 of FIG. 3 may generally include hardware and software configured to efficiently manage the overall operation of the surgical system 100. As shown, the computer system 106 may provide a computer 300 that is in communication with at least an input device 302 and a display device 304. The computer 300 may be in wired or wireless communication with one or more of the tracking device 102, the haptic device 104, the surgical tool 106 and the surgical device 200. The input device 302 may include a keyboard, a mouse, a trackball, a touch screen, a touch pad, a microphone, a dial, a switch, a button, a camera, or any other device suitable for inputting information directly into the computer 300. The display device 304 may include a liquid crystal display (LCD), a cathode ray tube (CRT) display, a plasma screen, a touch screen, and/or any other output device for visually interfacing with the computer 300. The computer 300 of FIG. 3 may further be in communication with, or have stored therein, medical images of the surgical volume 110, as obtained by CT devices, MRI devices, fluoroscopic devices, ultrasound devices, and the like. Based on the medical images, the computer 300 may generate two- or three-dimensional models of the surgical volume 110 which may further be graphically manipulated by the user via the input device 302 and viewed via the display device 304. The computer 300 may be configured to manage registrations between digitized points of anatomic surface as detected by the probe tip 216 and the two- or three dimensional models of the surgical volume 110. More specifically, based on data provided by the probe tip 216 and the associated position sensing device 108, the computer 300 may detect the actual pose of the anatomic region of interest relative to a common frame of reference within the surgical workspace, and manipulate the modeled image of the region of interest to correspond to the detected pose. In alternative embodiments, the models generated by the computer 300 may also include spatial mapping information pertaining to the regions of interest within the surgical volume 110. The computer 300 may integrate the mapped regions with the tracking information provided by the tracking device 102 and/or the haptic device 104 so as to generate and communicate the appropriate signals or control parameters to the haptic device 104, surgical tool 109, or the like.

The accuracy of the registration and the reliability of the computational representation of detected anatomic surfaces may thus rely significantly on the spatial relationship between the surgical device 200 and the position sensing device 108 as well as the consistency thereof throughout use of the surgical device 200. Moreover, in order to ensure proper integration between the digitized points of actual anatomic surfaces and digitized models of the anatomy, the position of the probe tip 216 relative to the position sensing device 108 must remain consistent for all detected anatomic surfaces within a given surgical volume 110. Accordingly, once the surgical device 200 is initially attached to the position sensing device 108, but prior to use, the surgeon may use the computer 300 to verify, or calibrate and verify, the probe tip 216 and its spatial relationship relative to the position sensing device 108. Once the initial calibration is complete, the surgeon may utilize the surgical device 200 as initially configured to probe the relevant anatomic surfaces within the surgical volume 110. However, some anatomic surfaces may be beyond the range of motion that is allowed by the surgical device 200 and may only be accessible by adjusting the probe 204. In order to make the adjustment, the surgeon may detach or simply loosen the handle 202 of the surgical device 200 from the position sensing device 108, and rotate the nonlinear connector of the probe tip 216 to a desired orientation. Once the desired rotational orientation is selected, the surgeon may reattach or tighten the handle 202 to the position sensing device 108. In alternative modifications, the surgical device 200 may be configured such that the probe 204 may be substantially free to rotate about one or more revolute joints disposed between the handle 202 and the position sensing device 108 such that the handle 202 does not need to be loosened or detached from the position sensing device 108 during adjustments without departing from previously calibrated specifications.

As the surgical device 200 of FIG. 4 is configured by design such that the probe tip 216 consistently remains on the center axis regardless of the rotational orientation of its associated nonlinear connector, a surgeon using the probe 204 may continue collecting positioning data of anatomic surfaces without recalibrating between adjustments. Further, because the initially calibrated spatial relationship between the probe tip 216 and the position sensing device 108, such as an array of optically detectable markers, is left undisturbed between adjustments, there is no need to calibrate the probe 204 for each adjustment.

Based on the foregoing, it can be seen that the present disclosure provides a simplified surgical device that facilitates MIS as well as other applicable surgical procedures.

While only certain embodiments have been set forth for the purposes of illustration, alternatives and modifications will be apparent from the above description to those skilled in the art. These and other alternatives are considered equivalents and within the spirit and scope of this disclosure and the appended claims.

What is claimed is:

1. A probe, comprising:
    a shaft portion rotatably attachable to a position sensing device;
    a nonlinear portion of fixed geometry that is at least partially removed radially outward from both an outer diameter and a center axis of the shaft portion, and selectably rotatable about the center axis to one of a plurality of rotational orientations; and
    a tip disposed at a distal end of the nonlinear portion and positioned on the center axis, the tip having a substantially constant position relative to the position sensing device, the tip including a sensing mechanism configured to generate electronic signals corresponding to changes in proximity of an anatomic surface relative to the tip.

2. The probe of claim 1, wherein the nonlinear portion is configured such that the tip aligns with the center axis independent of the orientation of the nonlinear portion.

3. The probe of claim 1, wherein the tip is adapted to collect positioning data of an anatomic surface.

4. The probe of claim 1, wherein the tip includes a digitizing point configured to digitize anatomic surfaces for registration to computationally represented anatomic surfaces.

5. The probe of claim 1, wherein the tip is configured as a sphere having a spherical center disposed on the center axis.

6. The probe of claim 1, wherein the tip is configured to receive an optoelectronic position transducer.

7. A surgical device, comprising:
    a handle rotatably attachable to a position sensing device; and
    a probe coupled to the handle, the probe comprising a nonlinear connector and a tip, the nonlinear connector being of fixed geometry that is at least partially removed radially outward from both an outer diameter and a center axis of the handle, and rotatable about the center axis to one of a plurality of rotational orientations, the tip having a substantially constant position relative to the position sensing device, the tip including a sensing mechanism configured to generate electronic signals corresponding to changes in proximity of an anatomic surface relative to the tip.

8. The surgical device of claim 7, wherein the nonlinear connector is bent at least once along a length thereof and the tip is configured to align with the center axis independent of the rotational orientation of the nonlinear connector.

9. The surgical device of claim 7, wherein the tip is configured as a sphere having a spherical center disposed on the center axis.

10. The surgical device of claim 7, wherein the handle is coupled to the position sensing device through a revolute joint and the rotational orientation of the nonlinear connector is selectable through rotation of the handle.

11. The surgical device of claim 10, wherein an initial calibration of the probe is maintained through a plurality of different rotational orientations.

12. The surgical device of claim 7, wherein the tip includes a digitizing point configured to digitize anatomic surfaces for registration to computationally represented anatomic surfaces.

13. The surgical device of claim 7, wherein the probe is fitted with an array of markers.

14. A surgical system, comprising:
    a position sensing device;
    a probe rotatably coupled to the position sensing device, the probe comprising a nonlinear connector and a tip having a sensing mechanism configured to collect positioning data from an anatomic surface and generate electronic signals corresponding to the positioning data, the nonlinear connector being of fixed geometry that is at least partially removed radially outward from both an outer diameter and a center axis of the probe, and rotatable about the center axis to one of a plurality of rotational orientations relative to the position sensing device, the tip having a substantially constant position relative to the position sensing device; and
    a computer system in communication with the probe, the computer system configured to receive the positioning data from the tip, and digitize points of the anatomic surface based on the positioning data.

15. The surgical system of claim 14, wherein the probe is configured such that the tip aligns with the center axis independent of the rotational orientation of the nonlinear connector.

16. The surgical system of claim 14, wherein the computer system is configured to register the digitized points of the anatomic surface to a computational representation of the anatomic surface based on the positioning data.

17. The surgical system of claim 16, wherein the computer system is configured to synchronize a spatial pose of the computational representation of the anatomic surface to an actual pose of the anatomic surface.

18. The surgical system of claim 14, wherein the position sensing device employs an array of markers to track the probe.

19. The surgical system of claim 14, wherein the position sensing device employs a mechanical tracking arm for tracking the probe.

20. The surgical system of claim 14, wherein the tip is configured as a sphere having a spherical center disposed on the center axis.

* * * * *